United States Patent [19]

Young

[11] 4,032,786

[45] June 28, 1977

[54] METHOD OF USING RESONANCE ATOMIC SCATTERING OF RADIATION TO MEASURE GASEOUS SPECIES

[75] Inventor: Robert A. Young, Loretto, Canada

[73] Assignee: Xonics, Inc., Van Nuys, Calif.

[22] Filed: Apr. 2, 1976

[21] Appl. No.: 672,974

Related U.S. Application Data

[63] Continuation of Ser. No. 562,221, March 26, 1975, abandoned.

[52] U.S. Cl. ............................... 250/373; 250/435; 356/85; 356/201
[51] Int. Cl.² ........................................ G01J 1/42
[58] Field of Search .......... 250/373, 393, 435, 461, 250/504; 356/85, 201

[56] References Cited

UNITED STATES PATENTS

| | | |
|---|---|---|
| 2,431,019 | 11/1947 | Barnes .............................. 250/344 |
| 2,974,227 | 3/1961 | Fisher et al. ........................ 250/373 |
| 3,190,172 | 6/1965 | Langberg .......................... 356/85 X |
| 3,198,721 | 8/1965 | Rich .................................. 250/373 |
| 3,829,696 | 8/1974 | Birnbaum .......................... 250/461 |
| 3,884,583 | 5/1975 | Kikuchi ............................ 356/85 X |
| 3,914,054 | 10/1975 | Hadeishi ............................. 356/85 |
| 3,970,430 | 7/1976 | Reader et al. ...................... 250/373 |

*Primary Examiner*—Harold A. Dixon
*Attorney, Agent, or Firm*—Harris, Kern, Wallen & Tinsley

[57] ABSTRACT

A device for measuring gaseous species which comprises a scattering chamber having a resonance lamp illuminating said chamber and a detector for measuring a scattered light within said chamber and conduit means for delivering said gaseous species to said chamber and a photofragmentation chamber within said conduit for selectively decomposing said gaseous species.

13 Claims, 1 Drawing Figure

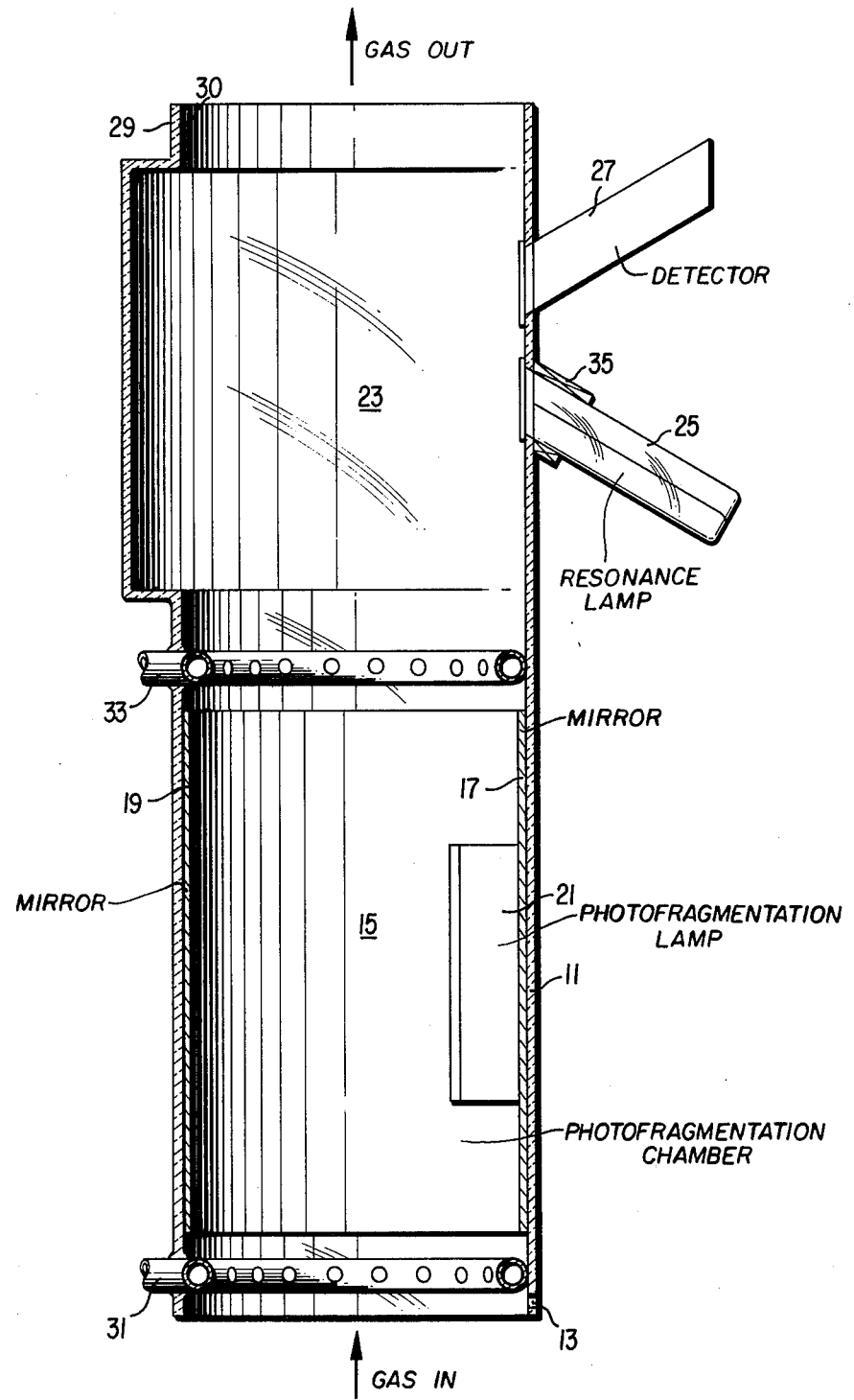

METHOD OF USING RESONANCE ATOMIC SCATTERING OF RADIATION TO MEASURE GASEOUS SPECIES

This is a continuation, of application Ser. No. 562,221, filed Mar. 26, 1975, now abandoned.

This application relates generally to the measurement of gaseous species and more particularly to the measurement of gaseous species by means of resonance scattering.

The concentration of metal atoms in a sample is often measured by dissolving the sample (with acids, for example), and spraying the solution into the fuel or oxidizer of a high temperature flame where the compounds containing the metal are thermally decomposed and the concentration of metal atoms in the flame is measured by their absorption or scattering of light, characteristic of the atom. Using standard solutions, containing known amounts of metal atoms, either free or in chemical combination, the measured light absorption or scattering can be calibrated, so that this procedure becomes a means of measuring very small amounts of metal atoms. This type of measurement is limited to the measurement of metal atoms.

The present invention increases the number of specific substances that can be measured directly by the resonance scattering technique, and includes species which can be measured directly by this technique in air, and provides a new means to decompose species, other than by thermal decomposition in flames, into constituents which, for a number of reasons, are preferred over the parent species, for measurement by resonance scattering techniques.

Resonance scattering or absorption can be used to measure atoms, other than metals and molecules. A use of radiation charateristic of atomic deuterium to measure the concentration of CO is outlined in patent application Ser. No. 453,164, filed Mar. 20, 1974 by the present inventor, and suitable sources of resonance radiation are detailed in U.S. Pat. No. 3,851,214 and U. S patent application filed Mar. 10, 1975 entitled Resonance Lamp Having a Triatomic Gas Source and filed in the name of the present inventor.

It is an object of this invention to provide a measurement of gaseous species by means of resonance scattering.

A further object of this invention is to provide a measurement of atoms of metals as well as gases.

Yet another object of this invention is to provide a measurement of gaseous species in air.

These and other objects of this invention will become obvious from the following description when taken in conjunction with the drawings wherein the single FIGURE is a schematic representation of the system of the present invention.

Turning now more specifically to the drawing, the gas containing species to be measured is either pushed into the inlet 13 of conduit 11 and eventually out of outlet 30 of conduit 29, or the gas is sucked into inlet 13 and out of outlet 30 by pumps, fans, etc. (not shown). The gas sample passes further gas inlet 31 into a photofragmentation section 15 whose walls are mirrored as at 17 and 19 and which contains a source of radiation 21 whose characteristics are chosen to effectively decompose the desired species while not decomposing other species present in the gas sample. The gas sample then passes gas inlet 13 and into a scattering chamber 23 where it is illuminated by resonance lamp 25 with a device 36 to generate a magnetic field to shift the frequency of the light emitted from the lamp and whose radiation is detected, after scattering in the gas sample, by detector 27. The gas finally leaves the apparatus through outlet 30.

Inlets 31 and 33 can be used to add gaseous species, which may be diluted in an inert gas, to calibrate or null the apparatus, and to chemically convert species in the gas sample into another species easier to measure. In relation to inlet 33, it may be used to effect a similar conversion on species produced in the photo fragmentation section 15. The scattering chamber must be so constructed that less light from lamp 25 reaches the detector from the walls of the chamber than is scattered into the detector 9 by the species in the gas sample. This can be accomplished by assuring that the surfaces and edges are smooth and by darkening all surfaces.

The simplest examples of the use of the apparatus of this invention are the measurement of H, D, Cl, OH, NO, by resonance scattering of their resonance radiation. Because $O_2$ and $N_2$ do not strongly absorb the resonance radiation characteristic of these species (1216 A, 1215 A, 1158 A, 3064 A, 2040 A) such measurements can be made in air. However, O, whose resonance lines are near 1300 A, cannot be measured in air, except at high altitude where the amount of $O_2$ has diminished sufficiently.

The addition of $NO_2$ through inlets 31 and 33 will chemically remove H and D, and O, the addition of NOCl will remove Cl; the addition of CO or HCl will remove OH, and the addition of $O_3$ will remove NO.

A more complicated use of the device involves adding a species through inlets 31 or 33 to convert one species into another. For example, the addition of CO to convert OH to H which produces

A measure of H is then a measure of OH.

Under some circumstances, HCl can be used in place of CO which produces

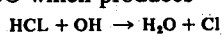

In this case, Cl may be measured. If the photolysis lamp is a mercury lamp designed to emit only the 2537 A line, CL0 will be selectively dissociated to Cl and O, and Cl is measured by resonance scattering and constitutes a measurement of ClO. Although ClO might be measured directly by resonance scattering, this indirect method may be superior, because a scattering chamber is generally not needed for measurements in air, since there is no background emission near the 1158 A resonance line of Cl.

Other chlorine containing gases likely to present in air do not absorb the 2537 A Hg line to any extent. Any other absorption, such as by $O_3$, is not strong and does not lead to the production of Cl. a 50 per cent absorption by a species not producing Cl could lead to at most a fifty per cent error, while a much smaller absorption leading to Cl production, could produce an order of magnitude error.

If the photolysis lamp is designed to produce the 1849 A mercury line then HCl will be strongly dissociated into H and Cl, both of which can be measured to give a measure of HCl, after calibration. Since $H_2O$ and hydrocarbons, $CH_4$ for example, may also be decomposed, a measure of H requires additional interpretation and auxiliary information if a measure of H is to be a valid measurement of HCl, or $H_2O$ or $CH_4$.

The 1849 A Hg line is strongly absorbed by $HNO_3$ to produce $OH + NO_2$ and a measure of OH could be a measure of $HNO_3$, after calibration and investigation of possible interference (from $H_2O$, for example).

A similar way of measuring $CH_4$ and/or $H_2O$ with greater sensitivity, is to use a Kr lamp emitting at 1236 A, since both $H_2O$ and $CH_4$ absorb at about one thousand times more strongly at this wavelength.

Using such a photolysis lamp, a measure of OH by resonance scattering would be a measure of $H_2O$ and a measure of H would be a measure of $CH_4$ and $H_2O$ which can be corrected for the $H_2O$ contribution, using the OH measurement.

Depending upon the gaseous species to be investigated, the resonance lamp may be designed to emit the following:

1. The resonance lyman alpha line of atomic hydrogen.
2. The lyman alpha resonance line of atomic deuterium.
3. The 1158 A resonance line of atomic chlorine.
4. The 1302, 4, 6 A resonance lines of atomic oxygen.
5. The 3064 A (O,O) band due to OH.
6. The (O,O)γ band of No at 2040 A.

In the above listed emissions, the detector may take the following forms:

1. A $MgF_2$ windowed NO filled Geiger counter.
2. A LiF windowed NO filled Geiger counter.
3. A filtered photomultiplier for passing either the (O,O) or (O,1) band.
4. A filtered photomultiplier for passing either the (O,O) band or the (O,1), (O,2), (O,3) band.

Further, a magnetic field means 35 may be added to the resonance lamp for obtaining a Zeman modulation of the frequency of emission of said lamp.

The above description and accompanying drawing are illustrative only in that particular structures and parts could be substituted without departing from the invention. Accordingly, the invention is to be limited only by the scope of the following claims.

What is claimed is:

1. A device for measuring gaseous species comprising
    a scattering chamber;
    a resonance lamp illuminating said chamber;
    a detector for measuring the scattered light within said chamber;
    conduit means for delivering said gaseous species to said chamber;
    a photofragmentation chamber within said conduit for selectively decomposing said gaseous species; and
    means for adding gaseous species to the gas in said conduit.

2. The device of claim 1 wherein the lamp emits the resonance Lyman alpha line of atomic hydrogen and said detector is a $MgF_2$ windowed NO filled Geiger counter.

3. The device of claim 1 wherein said lamp emits the Lyman alpha resonance line of atomic Deuterium and the said detector is a $MgF_2$ windowed, NO filld Geiger counter.

4. The device of claim 1 wherein said lamp emits the 1158 A resonance line of atomic chlorine and the detector is a LiF windowed NO filled Geiger counter.

5. The device of claim 1 wherein said lamp emits the 1302, 4, 6 a resonance lines of atomic oxygen and said detector is a $MgF_2$ windowed NO filled Geiger counter.

6. The device of claim 1 whereins said lamp emits the 3064 A (O,O) band due to OH and the detector is a filtered photomultiplier, said filter being selected to pass the desired band.

7. The device of claim 1 wherein said lamp emits the (O,O) γ band of NO at 2040 A and the detector is a photomultiplier filtered to detect the desired band.

8. The device of claim 1 further comprising a magnetic field in said resonance lamp for obtaining a Zeman modulation of the frequency of its emission.

9. The device claim 1 wherein said scattering chamber minimizes the return of lamp radiation to the detector due to scattering from the structure of said chamber.

10. The device of claim 1 wherein said photolysis lamp is a Hg lamp emitting 2537 A radiation only.

11. The device of claim 1 wherein said photolysis lamp is a Hg lamp emitting both the 2537 A and 1849 A line.

12. The device of claim 1 wherein said photolysis lamp is a 1236 Kr lamp.

13. The device of claim 1 further comprising
    at least one other gas inlet means between said conduit means and said scattering chamber.

* * * * *